(12) United States Patent
Byers et al.

(10) Patent No.: US 6,792,314 B2
(45) Date of Patent: Sep. 14, 2004

(54) MINIATURE IMPLANTABLE ARRAY AND STIMULATION SYSTEM SUITABLE FOR EYELID STIMULATION

(75) Inventors: Charles L. Byers, Canyon Country, CA (US); Kate E. Fey, Valencia, CA (US); Ralph M. Weisner, Woodland Hills, CA (US); Gary D. Schnittgrund, Granada Hills, CA (US)

(73) Assignee: Alfred E. Mann Foundation for Scientific Research, Valencia, CA (US)

( * ) Notice: Subject to any disclaimer, the term of this patent is extended or adjusted under 35 U.S.C. 154(b) by 251 days.

(21) Appl. No.: 10/160,804

(22) Filed: May 31, 2002

(65) Prior Publication Data

US 2003/0023297 A1 Jan. 30, 2003

Related U.S. Application Data

(60) Provisional application No. 60/299,379, filed on Jun. 18, 2001.

(51) Int. Cl.[7] ............................. A61N 1/05; A61N 1/18
(52) U.S. Cl. ......................... 607/53; 607/116; 607/141
(58) Field of Search ............................ 607/53, 54, 116, 607/117, 118, 141, 48

(56) References Cited

U.S. PATENT DOCUMENTS

| | | | |
|---|---|---|---|
| 4,799,487 A | 1/1989 | Bleicher | |
| 5,843,147 A | 12/1998 | Testerman et al. | |
| 5,917,346 A | 6/1999 | Gord | |
| 5,919,220 A | * 7/1999 | Stieglitz et al. | ............. 607/118 |
| 5,999,848 A | 12/1999 | Gord et al. | |
| 5,999,849 A | 12/1999 | Gord et al. | |
| 6,088,608 A | 7/2000 | Schulman | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,259,937 B1 | 7/2001 | Schulman et al. | |
| 6,315,721 B2 | 11/2001 | Schulman et al. | |

FOREIGN PATENT DOCUMENTS

| | | |
|---|---|---|
| EP | 0 033 643 A1 | 8/1981 |
| EP | 0 586 858 A1 | 3/1994 |
| WO | WO 93/20887 | 10/1993 |

* cited by examiner

*Primary Examiner*—Jeffrey R. Jastrzab
(74) *Attorney, Agent, or Firm*—Gary D. Schnittgrund

(57) ABSTRACT

An implantable miniature eyelid electrode apparatus that causes a paralyzed eyelid to close or open by passing an electrical stimulating current to a nerve or muscle, is comprised of a longitudinally flexible, nonconductive body containing electrodes that pass an electrical signal to the nearby nerve or muscle, which closes or opens the eyelid. The apparatus is electrically actuated by a source that may be located remotely from the apparatus. The electrical signal passes along wires from the source to the apparatus. The apparatus is biocompatible with the environment in the living tissue and is electrically insulated from the surrounding tissue, except where the electrodes contact the living tissue. The apparatus is very small and is not obvious to visual inspection when implanted.

35 Claims, 9 Drawing Sheets

MINIATURE IMPLANTABLE ARRAY AND STIMULATION SYSTEM SUITABLE FOR EYELID STIMULATION

This application claims the benefit of U.S. Provisional Application No. 60/299,379, filed Jun. 18, 2001.

FIELD OF THE INVENTION

This invention relates to a prosthetic medical device and methods, and more particularly to implantable eyelid devices and methods for controlling the opening and closing of an eyelid.

BACKGROUND OF THE INVENTION

Injury or neurological disorders, such as Bell's palsy, myasthenia gravis, and Lou Gehrig's disease (amyotrophic lateral sclerosis), cause one or both of the upper and/or the lower eyelids to droop and to stop their natural blinking. When this occurs the eye surface dries out, leading to pain and discomfort, infection, blindness, and possibly loss of the eye.

Traditional treatments for this condition include implanted eyelid weights or springs, lubricating eye drops, and surgical suturing or taping of the eyelids shut. Various disadvantages exist for each of these existing treatments, e.g., the use of implanted eyelid weights may cause the eyelid to open when opening is not desired.

The structure of the eyelid 56 is shown in FIG. 1. The muscle fibers of the orbicularis oculi 50 surround the palpebral fissure, which is the slit between the upper and lower lids. The function of the orbicularis oculi 50 is to close the eye. The palpebral part 52 sweeps in curves in the upper and lower eyelids. On contraction, the eyelids are closed gently. The orbital part 54 sweeps in concentric curves in the forehead and cheek as a flat, thin sheet of muscle. Contraction lowers the eyebrow, and when this muscle contracts with the palpebral part 52, the eyes are squeezed tightly shut. The orbicularis oculi 50 can fail to contract in a damaged, partially denervated eyelid, thus there is a loss of eyelid blinking.

The levator palpebrae superioris 58 functions to elevate the upper eyelid, thus opposing the orbicularis oculi 50 muscle. The frontalis-occipitalis 60 elevates the eyebrows and is a dilator of the palpebral fissure.

Depending on the cause of the inability to close or open an eyelid, one possible solution is to stimulate the muscle or nerve of the nonfunctioning eyelid. A number of approaches have been proposed, such as in U.S. Pat. Nos. 4,799,487 and 5,843,147. U.S. Pat. No. 5,843,147 presents an implantable electrode approach to solving this problem. For any such stimulus system to be efficiently utilized, the electrode for the system must be designed such that it can be easily implanted, is chronically stable once implanted, and provides electrical stimulation without causing pain to the patients. For example, it is important to avoid stimulation of surrounding facial muscles or nearby sensory nerves. Current known electrodes do not provide all of such functionality as applicable to the eyelid, eye, and surrounding area.

It is well known that electrical stimulation of the retina may have a beneficial effect on certain degenerative eye diseases. For example, U.S. Pat. No. 6,275,735 describes normal retinal cell function as a photochemical reaction converting light energy to an electrical impulse that travels to the brain and vision occurs. With age-related macular degeneration (AMD) and other visual system diseases, diseased, inflamed retinal cells eventually lose cell function. Adenosine triphosphate (ATP) levels drop, protein synthesis drops, the electrical resistance goes up, and cell membrane electrical potential goes down. The cells may go dormant for a time before they die. If electrical stimulation is provided to the cells before they die, blood vessel permeability is increased, a more normal cellular electrical potential will be achieved, the ATP levels will increase, protein synthesis will occur again, and normal cell metabolism will be restored. In addition, electrical stimulation appears to have a healing effect on the small blood vessels in the retina, promoting a more efficient delivery of nutrients to the retinal cells and a more efficient uptake of proteins that can accumulate on the retina. Thus, microcurrent stimulation will help rejuvenate the cells in the retina to slow or stop degeneration of the eye due to AMD. With the proper microcurrent stimulation waveform and therapy procedures, AMD may be slowed or stopped in a large number of people suffering from the disease.

For the reasons indicated above and for other reasons which will become apparent from the detail below, improved implantable eyelid electrode devices and methods of implanting such devices are needed. It is therefore the object of the present invention to provide such electrodes and to provide methods for closing or opening an eyelid by closed or open loop methods.

SUMMARY OF THE INVENTION

The apparatus of the instant invention is an implantable miniature stimulator and/or sensor for eyelids. The device is surgically implanted on or near a nerve or muscle that controls the blinking function of an eyelid. Electrical pulses are transmitted from a control device that may be located remotely from the stimulator, and which may be implanted in the body. The stimulating electric pulses travel along an electrically insulated cable that contains a number of very small diameter wires. The wires pass through an electrically insulating silicone body and down a leaflet body where they are attached to an electrode. The electrode rests on the nerve or muscle to be stimulated.

In an open loop control case, an electrical stimulating pulse is transmitted to the electrodes, at intervals on the order of several times per minute, which causes the paralyzed eyelid to open or close for normal blinking. Alternatively, the feedback signal in a closed loop control case may be generated in response to a sensor on a functional eyelid, responsive to a neurostimulator muscular signal, which is then used to trigger stimulation of the paralyzed eyelid. In both cases, the input stimulation signal may be adjusted to give a satisfactory and consistent response.

OBJECTS OF THE INVENTION

It is an object of the invention to provide an implantable miniature array suitable to cause an eyelid to blink.

It is an object of the invention to provide an implantable miniature array.

It is an object of the invention to provide a biocompatible miniature implant that is connected by an electrical connection to a remote control device.

It is an object of the invention to provide a method of controlling the opening and closing of a non-functioning eyelid with a signal from the functioning eyelid.

It is an object of the invention to provide a closed loop method of controlling the stimulating array signal.

Other objects, advantages and novel features of the present invention will become apparent from the following detailed description of the invention when considered in conjunction with the accompanying drawings.

DETAILED DESCRIPTION OF THE PREFERRED EMBODIMENTS

The following description is the best mode presently contemplated for carrying out the invention. This description is not to be taken in a limiting sense, but is made merely for the purpose of describing the general principles of the invention. The scope of the invention should be determined with reference to the claims.

Figure 1:
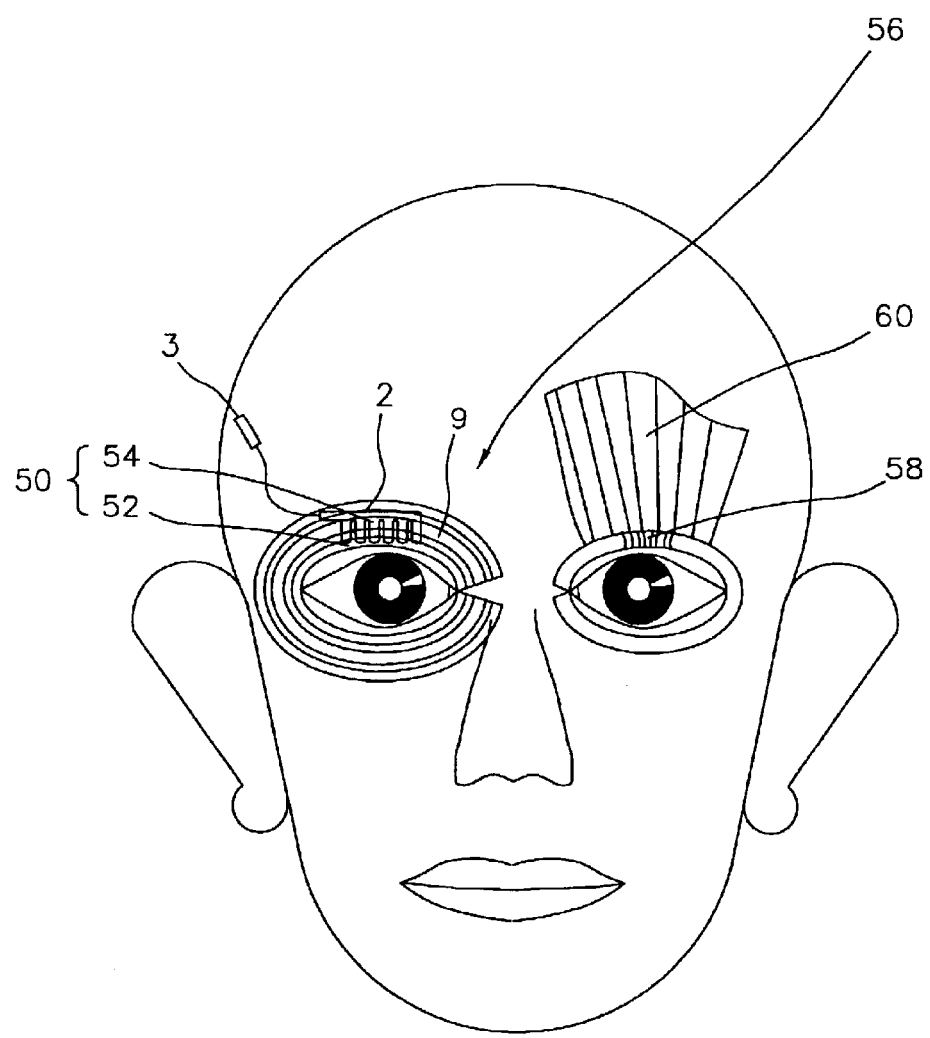
FIG. 1 illustrates the structure of the human eyelid.

FIG. 1 illustrates relevant facial muscles relating to eyelid stimulation. An eyelid stimulator 2 and a controller 3 are illustrated in a preferred implant orientation to a paralyzed eyelid 9.

Figure 2:
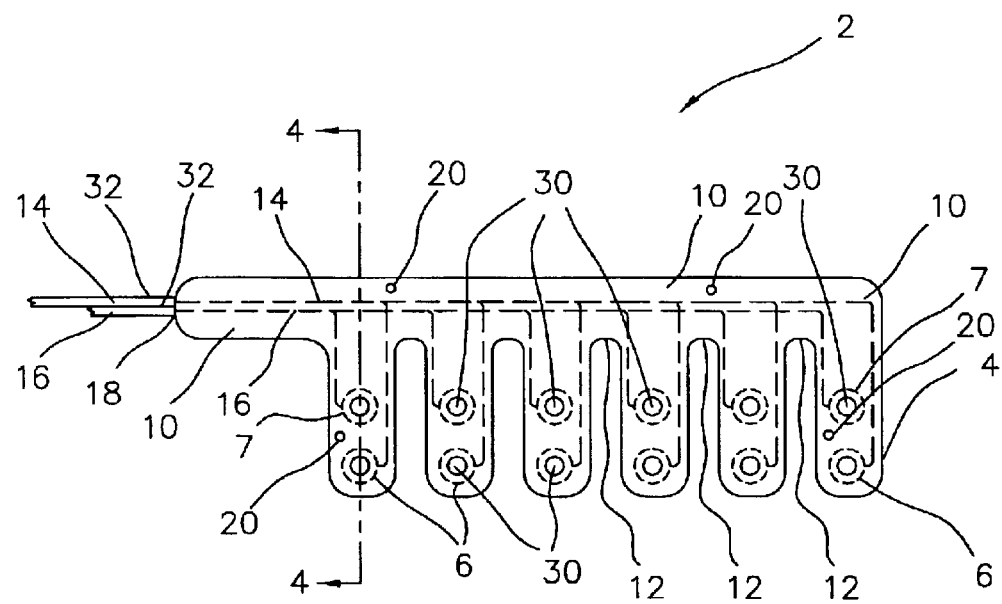
FIG. 2 illustrates a top view of the eyelid stimulator.
Figure 3:
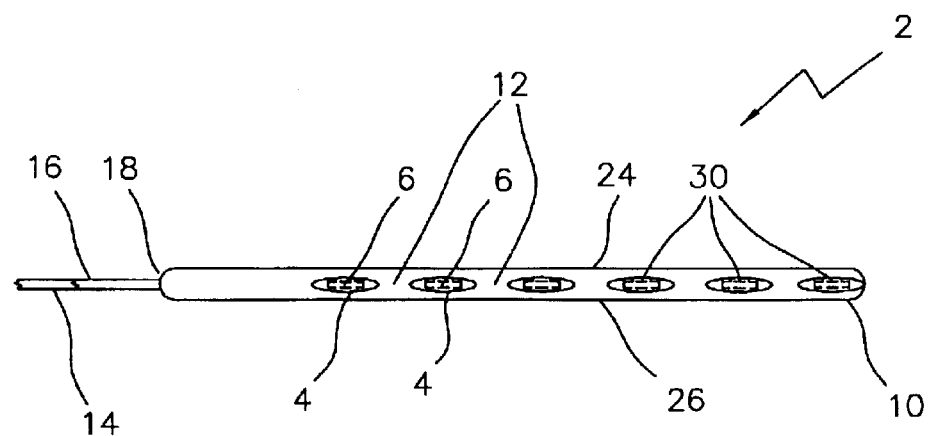
FIG. 3 illustrates a side view of the eyelid stimulator of FIG. 2.

Implantable eyelid stimulator 2 is generally illustrated in FIG. 2. In a preferred embodiment, the overall approximate dimensions of the eyelid stimulator 2, excluding insulated signal cable bundle 14 and insulated neutral cable bundle 16, are less than about 20 mm in length by less than about 10 mm in width, and, as shown in FIG. 3, less than about 0.50 mm in thickness. The eyelid stimulator 2 contains an electrode array. Leaflet bodies 4 hold electrically conductive signal electrodes 6 and neutral electrodes 7 that contact a nerve or a muscle that is to be stimulated. The signal electrodes 6 pass a stimulating electrical signal to the nerve or muscle, with the neutral electrodes 7 also contacting the nerve or muscle, thereby completing the stimulation circuit.

It is well known that when a muscle or nerve is electrically stimulated, alternating charge and discharge cycles must be employed to ensure that the muscle continues to respond to the stimulus. Therefore, the terminology of "neutral electrode" and "signal electrode" is arbitrary, because the neutral electrodes 7 and the signal electrodes 6 will preferably be reverse biased on each cycle.

Additionally, the eyelid stimulator 2 may be used as a sensor to detect signals and to transmit these signals to a remotely located signal receiver and processor. The eyelid stimulator 2 is similar to those disclosed in U.S. Pat. Nos. 6,315,721 and 6,208,894, which are incorporated in their entirety by reference herein. A feature of this preferred embodiment is the flexibility of leaflet bodies 4, which are free to move with the eyelid and the stimulated muscle. The signal electrodes 6 and the neutral electrodes 7 are located in the leaflet body 4. Apertures 30 are located in one surface of the leaflet body 4 to expose the signal electrodes 6 and the neutral electrodes 7 to the living tissue, thereby allowing electrical contact between the living tissue and the signal electrodes 6 and the neutral electrode 7.

Electrode lead body 10, FIG. 2, is joined to the leaflet bodies 4 such that a joint 12 is formed between the leaflet bodies 4, near the attachment of the leaflet bodies 4 and the electrode lead body 10. Anchor holes 20 in the electrode lead body 10 or leaflet bodies 4 preferably provide locations where attachments, such as sutures, may be placed for anchoring the eyelid stimulator 2. Alternately, living tissue may grow into the anchor holes 20, forming an attachment to the living tissue.

The insulated signal cable bundle 14 and the insulated neutral cable bundle 16, shown in FIG. 2, are each connected to a remotely located implanted miniature electric generator 66 (see FIG. 7) that produces electrical impulses that in turn stimulate the nerve or muscle that causes the eyelid to blink. The electric generator 66 could be a microstimulator or it could be another type of stimulator. The strands of wire comprising the insulated signal cable bundle 14 or insulated neutral cable bundle 16 are made of a highly conductive metal that is benign in the body, such as MP35N, stainless steel, iridium or an alloy of iridium, platinum or an alloy of platinum, such as platinum-iridium. Preferably, each strand of the wire has a diameter of approximately 0.001 inches. In a preferred embodiment, insulated signal cable bundle 14 and insulated neutral cable bundle 16 are comprised of approximately 19 strands of platinum-20 weight percent iridium wire. The insulated signal cable bundle 14 and the insulated neutral cable bundle 16 are electrically isolated from each other and from the environment in the living tissue by electrical insulation 32, which is preferably an outer covering of Teflon®, a registered trademark of E.I. du Pont de Nemours and Company, Wilmington, Del.

In the preferred embodiment, shown in FIGS. 2 and 3, there are approximately six leaflet bodies 4, each containing one signal electrode 6 and one neutral electrode 7. The signal electrodes 6 and the neutral electrodes 7 are made of a biocompatible material, such as stainless steel, iridium or an alloy of iridium, platinum or an alloy of platinum, such as platinum-iridium, and in a preferred embodiment, they are platinum-10 weight percent iridium. Typically, the signal electrodes 6 and the neutral electrodes 7 are essentially identical physically and are approximately 0.50 mm thick and 0.80 mm in diameter. While the signal electrodes 6 and the neutral electrodes 7 are shown in FIGS. 2 and 3 with the preferred round shape, the signal electrodes 6 and the neutral electrodes 7 may be of any shape, for example, rectangular, square, oval, or round, etc.

The eyelid stimulator 2 of FIGS. 2 and 3 is preferably oriented in the eyelid such that the leaflet bodies 4 lay across the orbicularis oculi muscle 50 (see FIG. 1). Accordingly, as the muscle contracts due to the applied electrical stimulation, the flexible leaflet bodies 4 of the present invention move freely with the muscle.

FIG. 3 illustrates the eyelid stimulator 2 from a side view and illustrates the insulated neutral cable bundle 16 entering the electrode lead body 10 at seal 18. The electrode lead body 10 is comprised of a top layer 24 and a bottom layer 26 that are joined together. The joint 12 is formed where the leaflet bodies 4 join the electrode lead body 10.

Figure 4:
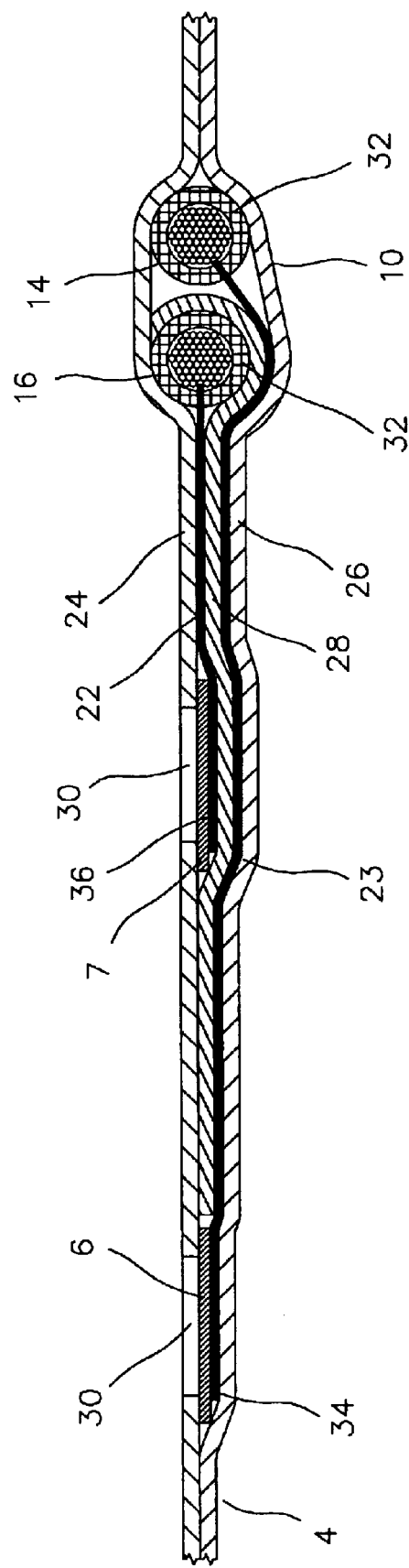
FIG. 4 illustrates a cross-sectional view of the stimulating and neutral electrodes of the eyelid stimulator through section 4—4 of FIG. 2.
Figure 5:
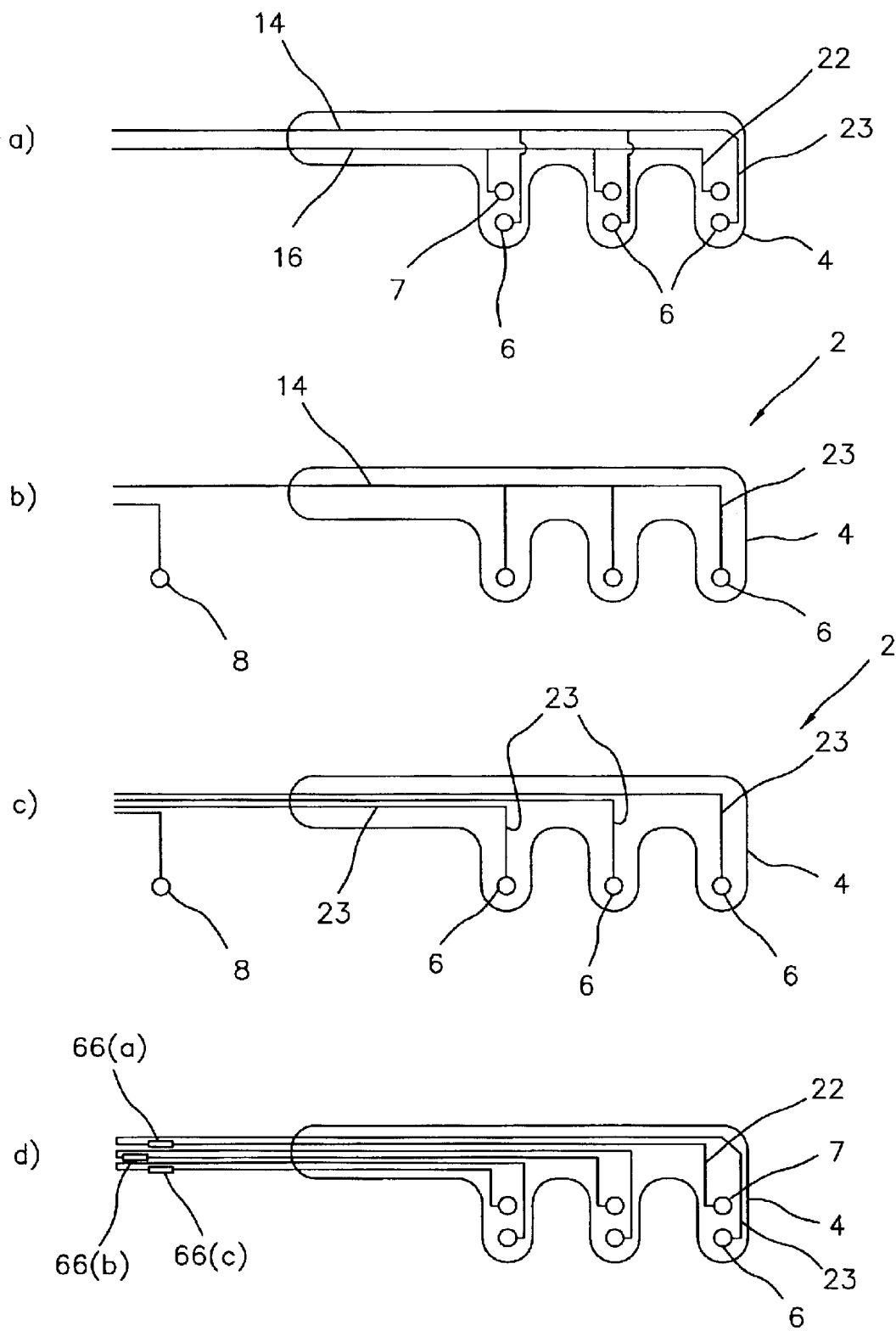
FIG. 5 illustrates simplified top view electrode connection schemes.

In the preferred embodiment shown in FIG. 4, where FIG. 4 is the view defined by section 4—4 of FIG. 2, signal lead wires 23 of the insulated signal cable bundle 14 are not insulated from each other. Hence, the insulated signal cable bundle 14 and all of the signal electrodes 6, attached thereto, are stimulated simultaneously. Similarly, all of the neutral lead wires 22 of the insulated neutral cable bundle 16 are connected together and are connected to the neutral electrodes 7. All neutral electrodes 7 are therefore at the same neutral voltage. FIG. 5a illustrates a simplified view of the electrodes connection scheme, where the signal electrodes 6 operate in unison and where the neutral electrodes 7 operate in unison.

FIG. 5b illustrates a simplified view of the electrodes connection scheme, where an alternative embodiment preferably has a common insulated signal cable bundle 14 that is connected to all of the signal electrodes 6 in the leaflet bodies 4. At least one ground electrode 8, which may be located remote from the eyelid stimulator 2, is in electrical contact with the living tissue. The ground electrode 8 is utilized to complete the circuit.

FIG. 5c illustrates a simplified view of the electrodes connection scheme, where a further alternative embodiment preferably has the individual signal electrodes 6 each connected to the individual signal lead wires 23, such that each signal electrode 6 may be individually powered and controlled. The ground electrode 8 may be either locally mounted in the eyelid stimulator 2 or in contact with the living tissue remote from the eyelid stimulator 2.

FIG. 5d illustrates a simplified view of the electrodes connection scheme, where a further alternative embodiment is described as bipolar pairs, which preferably has individual signal electrodes 6 each connected to individual signal lead wires 23, such that each signal electrode 6 may be individually powered. Each signal electrode 6 is paired with a neutral electrode 7, forming a bipolar pair. This bipolar pair is powered by an electric pulse generator, such as the implanted miniature electric generator 66, where generator 66a powers one bipolar pair, generator 66b powers a second bipolar pair, etc. It is obvious that one electric generator 66 may power sequentially or simultaneously one or any combination of bipolar pairs.

While there are numerous schemes for arranging the various electrodes, which may include signal electrodes 6, neutral electrodes 7, and/or ground electrodes (not illustrated), the preferred manner of arranging the neutral electrodes 7, shown in FIG. 4, is to attach each neutral electrode 7 to a separate neutral lead wire 22, that in turn passes along and through the leaflet body 4, along and through lead body 10, through seal 18 (see FIGS. 2 and 3), and into insulated neutral cable bundle 16. It is obvious that more than one neutral electrode 7 can be attached to the neutral lead wire 22.

The signal electrodes 6 are attached to the separate signal lead wire 23 that passes through the leaflet bodies 4 and along the lead body 10, through the seal 18, and into the insulated signal cable bundle 14. The lead body 10 is comprised of the top layer 24 and the bottom layer 26.

The leaflet bodies 4 and the electrode lead body 10 are preferably made of a biocompatible material that is electrically insulating. In a preferred embodiment, the biocompatible material is silicone having a hardness of about 70 on the Shore A scale as measured with a durometer. The insulated signal cable bundle 14 and insulated neutral cable bundle 16 pass through the seal 18, which is attached to the electrode lead body 10. The seal 18 is preferably made of silicone. In an alternative embodiment, the electrode lead body 10 and the leaflet bodies 4 are comprised of a biodegradable material that is resorbed by the body post-implantation. It is obvious that the insulated signal cable bundle 14 and the insulated neutral cable bundle 16 may be combined into one cable bundle.

An alternative method (not illustrated) of making the eyelid stimulator 2 is to utilize a flexible substrate on which a circuit is printed on one surface that is conformal-coated using biocompatible materials. The electrical contact points are made by placing holes through the substrate. Alternatively, contact points may be made by masking the conformal coating or photolithographically patterning the conformal coating.

The signal electrodes 6 are preferably attached by welding to the signal lead wire 23 at signal bond joint 34. Similarly, the neutral electrodes 7 are attached by welding to the neutral lead wire 22 at neutral bond joint 36.

The leaflet bodies 4 are comprised of the top layer 24 and the bottom layer 26, which are bonded together (see FIG. 4). Sandwiched between the top layer 24 and the bottom layer 26 is a separation layer 28. The separation layer 28 is preferably comprised of an electrically insulating material that is soft and biocompatible. In a preferred embodiment, the separation layer 28 is silicone having a hardness of about 70 on the Shore A scale as measured with a durometer.

Figure 6:
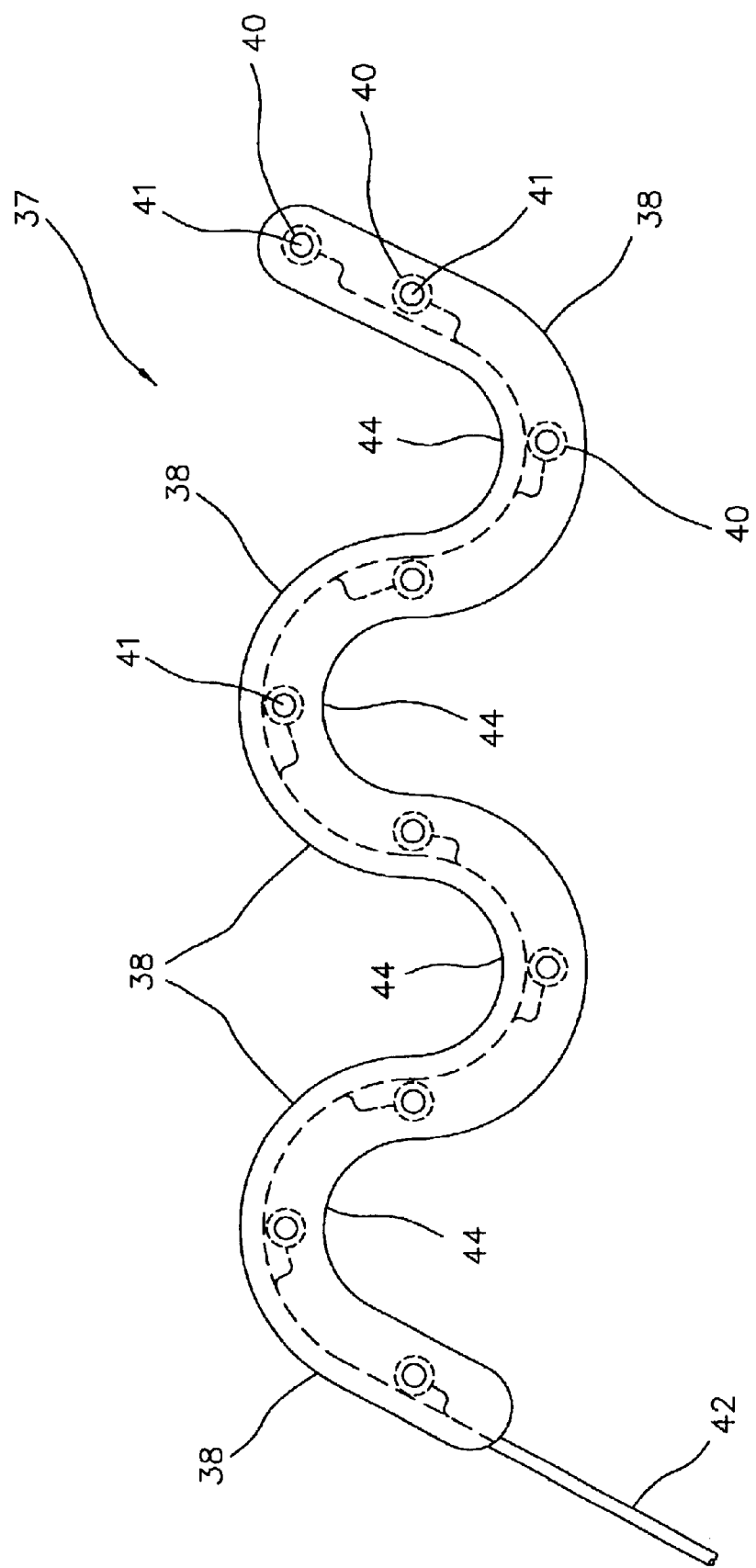
FIG. 6 illustrates a top view of an alternative eyelid stimulator.

FIG. 6 illustrates an alternative embodiment of an eyelid stimulator 37, wherein flexible leg electrodes 40 are contained within flexible legs 38. The eyelid stimulator 37 has a generally sinusoidal shape with rounded ends. The flexible legs 38 are connected by flexible joints 44, which provide flexibility for the apparatus to conform to the eyelid while maintaining electrical contact with the living tissue as it moves during muscle contraction. The flexible leg electrodes 40 are located with apertures 41 in the flexible legs 38. The flexible leg electrodes 40 make contact with the nerve or muscle tissue that is to be stimulated by contacting it through the apertures 41 in the flexible legs 38. Preferably, the flexible leg 38 is made of a material, such as silicon, which has a hardness of about 25 on the Shore A scale as measured with a durometer. The eyelid stimulator 37 is very flexible, allowing it to move and flex with the muscle as it responds to the electrical stimulation. An advantage of this embodiment is that the eyelid stimulator 37 is very soft and flexible, easily conforming to the shape of the eyelid.

The eyelid stimulator 37 is preferably oriented in the eyelid such that the flexible legs 38 lay across the orbicularis oculi muscle 50 (see FIG. 1). As the orbicularis oculi muscle 50 contracts due to the applied electrical stimulation, the flexible legs 38 move freely with the muscle.

The flexible leg electrodes 40 may be positive, negative, or neutral biased, depending upon which wire in cable bundle 42 is attached to the flexible leg electrodes 40.

Figure 7:
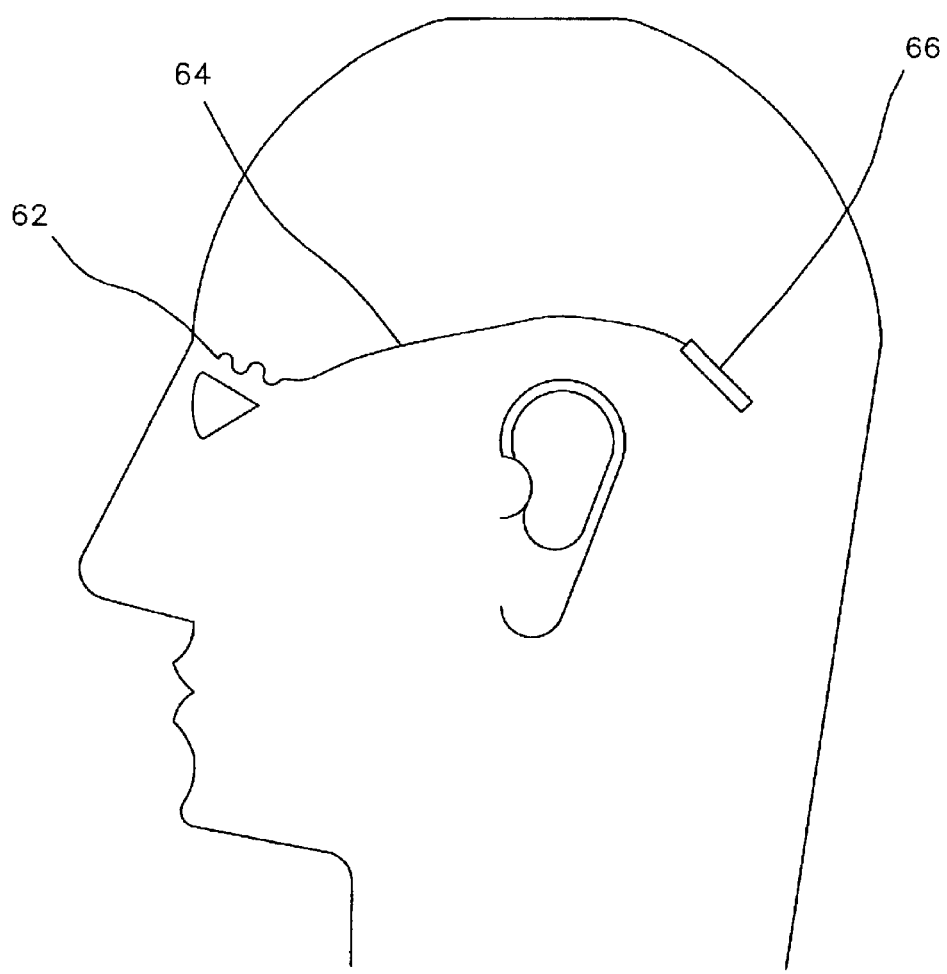
FIG. 7 illustrates the implanted eyelid stimulator connected to an implanted miniature electric generator.

FIG. 7 illustrates an exemplary open loop control system of the present invention wherein an implanted eyelid stimulator 62 is located in an eyelid. The implanted miniature electric generator 66 is located in an implanted position under the skin of the patient near the implanted eyelid stimulator 62 and connected to it by a transmission wire 64. In this system, the implanted miniature electric generator 66 is controlled by internal programming to generate an electric pulse on a programmed schedule at regular or irregular intervals. In an alternate embodiment, the implanted miniature electric generator 66 may receive an electric signal from a remote controller (not illustrated) to generate an electric pulse. Examples of known pulse generators are disclosed by U.S. Pat. Nos. 6,185,452; 6,208,894; and 6,315,721. A further alternative embodiment combines the controller with the implanted eyelid stimulator 62. This embodiment is not illustrated. The controller, exemplified by electric generator 66, is mounted on and therefore is a part of eyelid stimulator 62. More than one stimulator 62, having a controller integrally mounted thereon, may be connected with other similar stimulators 62. Known examples of miniature electric pulse generators are disclosed in U.S. Pat. No. 5,999,848, incorporated in its entirety by reference herein, which describes an implantable sensor/stimulator connectable to a controller.

Figure 8:
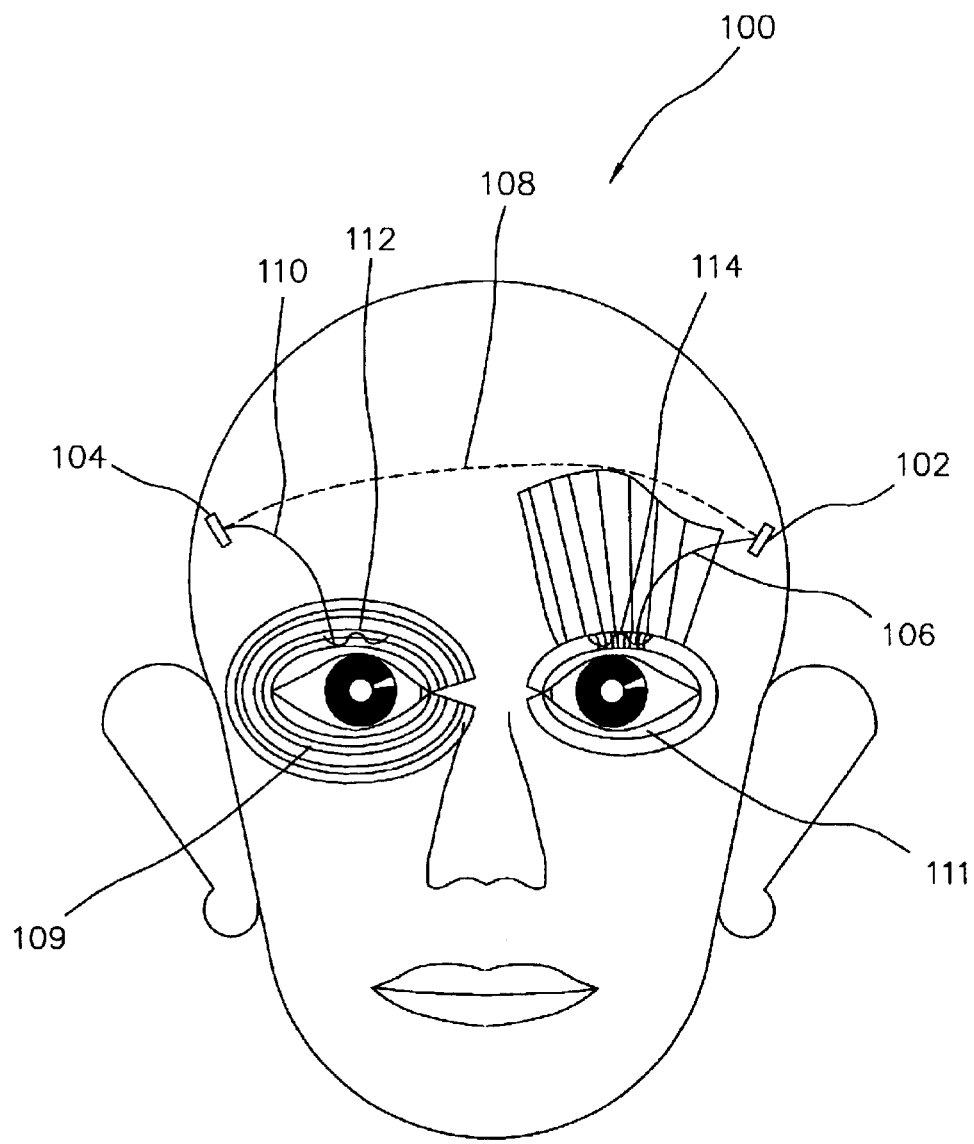
FIG. 8 illustrates a control scheme for an eyelid stimulator.

FIG. 8 illustrates an exemplary open loop control scheme 100 that coordinates stimulation between a functioning eyelid 111 and a paralyzed eyelid 109 via an implanted eyelid stimulator 112, located in the paralyzed eyelid 109. The implanted eyelid stimulator 112 is controlled by an implanted miniature electric pulse generator 104 via a transmission wire 110. The electric pulse generator 104, transmission wire 110, and eyelid stimulator 112 in combination form a stimulating device. Known examples of miniature electric pulse generators are disclosed in U.S. Pat. Nos. 6,164,284; 6,185,452; 6,208,894; and 6,315,721, each of which is incorporated in its entirety by reference herein.

In the open loop control scheme 100 of FIG. 8, a control signal is generated by the functioning eyelid 111, which is detected by an implanted eyelid sensor electrode 114 (similar in structure to that of eyelid stimulator 112) that is located in the muscle of the functioning eyelid 111. The electrical signal is transmitted by a sensor wire 106 to a control microsensor 102 which, when it receives the signal indicating that the functioning eyelid 111 has closed, sends an electric signal to the implanted miniature electric pulse generator 104 via the connection 108, thereby causing a signal to be generated by the implanted miniature electric pulse generator 104 to the eyelid stimulator 112, which causes the paralyzed eyelid 109 to close. The control microsensor 102, sensor wire 106, and eyelid sensor electrode 114 in combination form a sensing device. Obviously, the implanted eyelid stimulator 112 may be located on the nerves or on the muscles to cause the eyelid to open or to close. The miniature electric pulse generator 104 and control microsensor 102 are typical of the miniature monitoring and/or stimulating devices for implantation in living tissue disclosed by Schulman et al. (U.S. Pat. No. 6,164,284), Schulman et al. (U.S. Pat. No. 6,185,452), and Schulman et al. (U.S. Pat. No. 6,208,894), each of which is incorporated in its entirety by reference.

Alternatively, the connection 108 between the control microsensor 102 and the implanted miniature electric pulse generator 104 may be sent by wireless means, such as by RF signals, propagated radio signals, or alternating magnetic fields. An embodiment using a connection 108 that is wireless, simplifies the implantation process by eliminating implantation of a wire.

Figure 9:
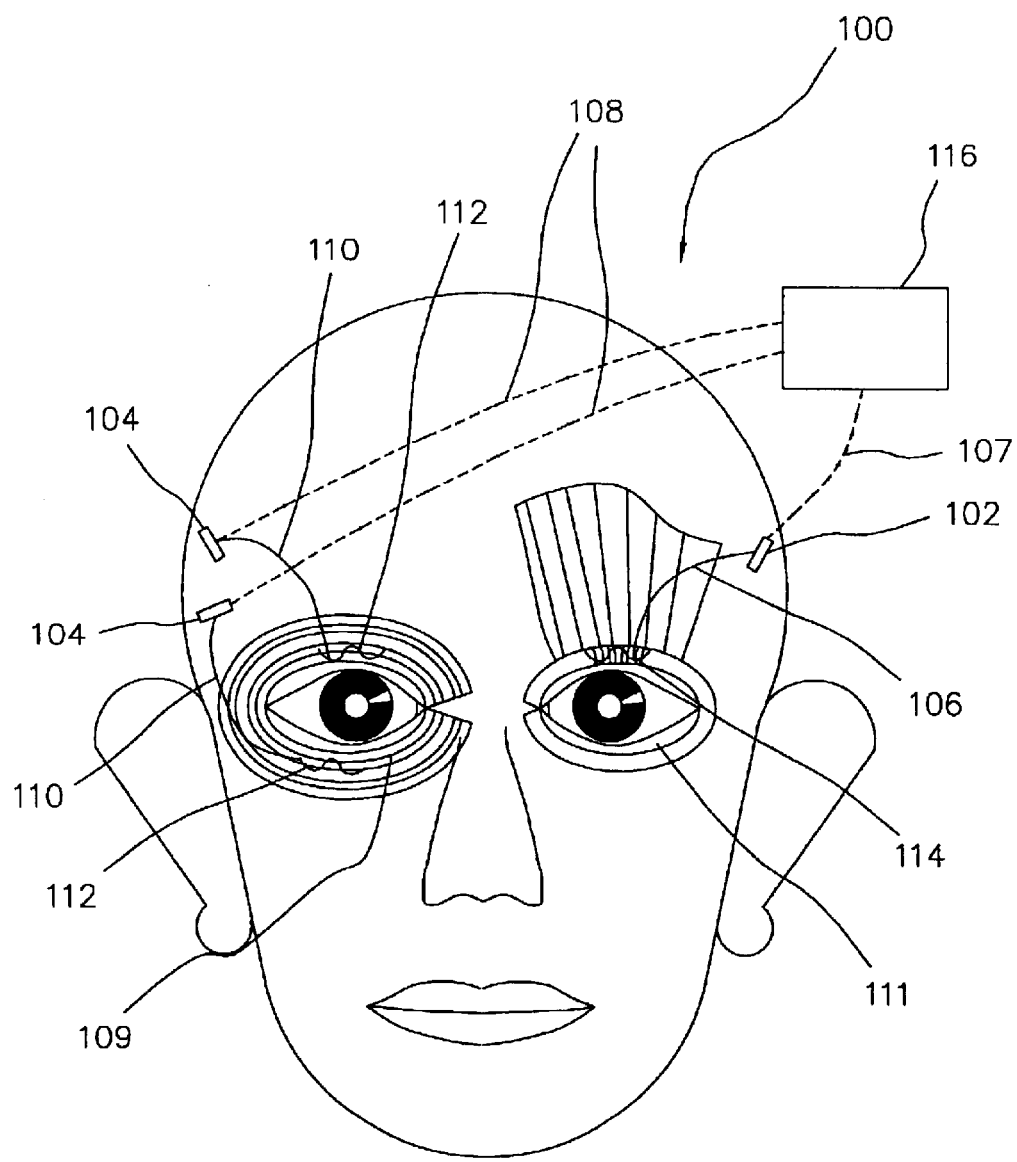
FIG. 9 illustrates a master control scheme for an eyelid stimulator.

In a further alternate embodiment (see FIG. 9), the open loop control scheme 100 is illustrated wherein a master control unit 116 may control one or more implanted miniature electric pulse generators 104, to control opening and/or closing of the paralyzed eyelid 109 in a timing sequence determined by the master control unit 116. This approach is useful to, but not limited to, applications when both eyelids are paralyzed. FIG. 9 illustrates an embodiment where there is one paralyzed eyelid 109 and one functioning eyelid 111. Closing the functioning eyelid 111 causes an electric signal to be generated that triggers the implanted eyelid pulse generators 104 to close the paralyzed eyelid 109. In this embodiment, the signal from the muscle of the functioning eyelid 111 is preferably detected by implanted eyelid sensor electrode 114 and sent to control microsensor 102 by sensor wire 106, which in turn transmits a signal by connection 107 to the master control unit 116. Connection 107 may be a wire or an RF signal, propagated radio signal, or alternating magnetic field. The master control unit 116 initiates a signal to the implanted miniature electric pulse generators 104, which send a signal to the implanted eyelid stimulator 112 by transmission wire 110, which is implanted in the paralyzed eyelid 109. The control microsensor 102, sensor wire 106, and eyelid sensor electrode 114 in combination form a sensing device. The electric pulse generator 104, transmission wire 110, and eyelid stimulator 112 in combination form a stimulating device. While two implanted miniature electric pulse generators 104 are illustrated, each of which is connected to one implanted eyelid stimulator 112, it is obvious that there may be either one or several miniature electric pulse generators 104 activated in response to signals from the master control unit 116. There may also be more than one implanted eyelid stimulator 112 connected to each of the implanted miniature electric pulse generators 104. The control signal to the implanted miniature electric pulse generators 104, that is generated by the master control unit 116, travels along connections 108, which may be a wire or an RF signal, propagated radio signal, or alternating magnetic field.

Figure 10:
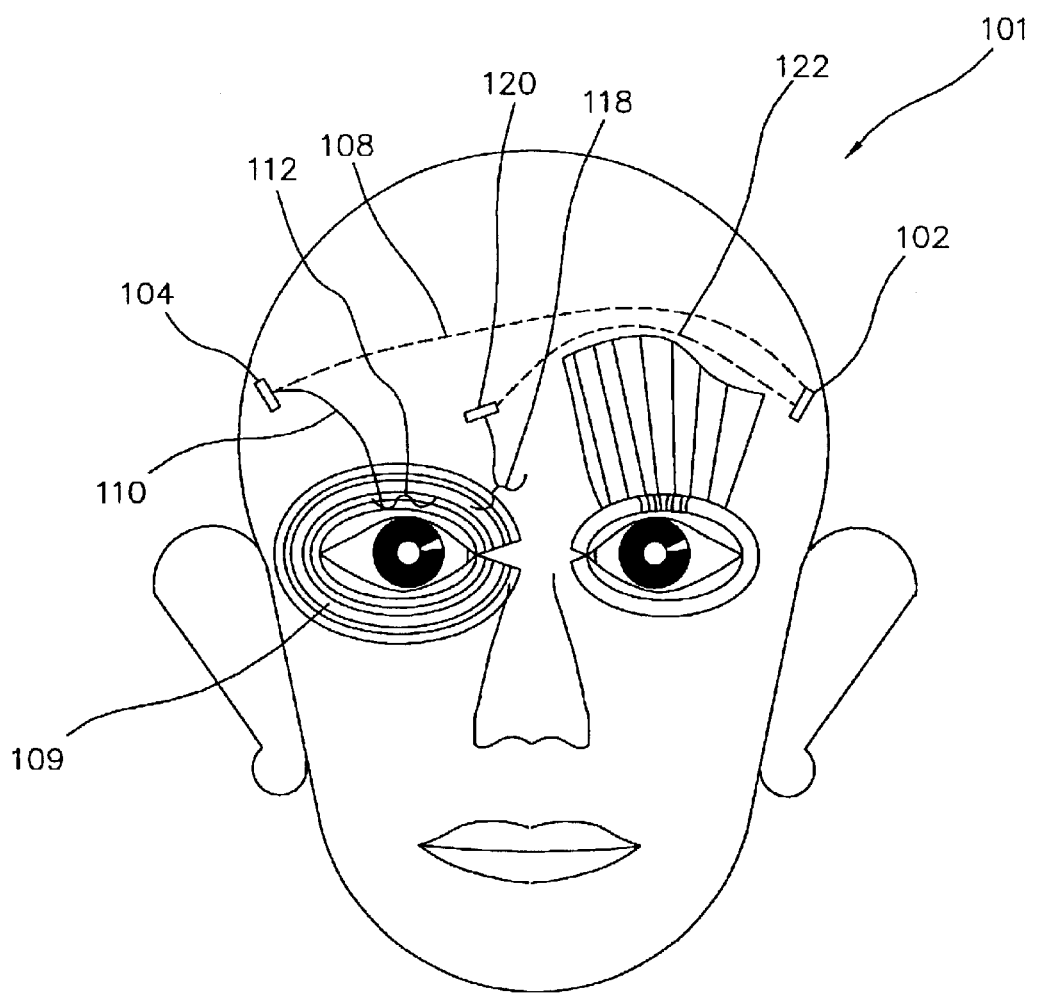
FIG. 10 illustrates a closed loop control scheme for an eyelid stimulator.

A further embodiment (see FIG. 10) is a closed loop control scheme 101 that uses a signal from the paralyzed eyelid 109, which is preferably detected by an implanted eyelid sensor electrode 118 to modify the electric signal that closes the paralyzed eyelid 109. For example, if the paralyzed eyelid 109 fails to close properly, then the electric pulse is increased (in amplitude and/or duration) to properly stimulate the eyelid 109 to close. The electric feedback signal is generated when the paralyzed eyelid 109 closes. Eyelid closure is detected by implanted eyelid sensor electrode 118 and is transmitted to an implanted miniature electric pulse sensor 120. A signal is then transmitted to the control microsensor 102 via a connection 122. The connection 122 may be a wire or a wireless signal, such as an RF link. The signal that is sent from the control microsensor 102 to the implanted miniature electric pulse generator 104 via connection 108 is preferably modified to attain the desired response of the paralyzed eyelid 109 to the electric signal from the implanted miniature electric pulse generator 104. U.S. Pat. No. 6,164,284 discloses a known closed loop control scheme. Alternately, the feedback may be sent to multiple master controllers rather than to a single controller. Numerous feedback loops from numerous stimulation sites may exist to achieve the desired result.

A further embodiment is to use the eyelid stimulator 2 (FIG. 1) to transmit electrical signals as a therapeutic electrical stimulator. Electrical stimulation of the retina may have a beneficial effect on certain degenerative eye diseases, e.g., age-related macular degeneration (AMD). By virtue of having the eyelid stimulated, the additional benefit of therapeutic electrical stimulation to the eye and/or the retina can be achieved.

Obviously, many modifications and variations of the present invention are possible in light of the above teachings. It is therefore to be understood that, within the scope of the appended claims, the invention may be practiced otherwise than as specifically described.

What is claimed is:

1. An implantable electrode apparatus suitable for providing or sensing signals from an eyelid, said apparatus comprisisng:

a body of a formed flexible material;

at least one flexible leg portion of said body;

at least one electrically conductive electrode that is contained within said at least one flexible leg portion;

at least one lead wire in electrical contact with said conductive electrode wherein said lead wire is attached to said conductive electrode; and a controller mounted on said body.

2. The implantable electrode apparatus according to claim 1 wherein said body of formed flexible material comprising silicone having a hardness of about 70 or less on the Shore A scale as measured with a durometer.

3. The implantable electrode apparatus according to claim 1 wherein said at least one flexible leg portion comprising silicone having a hardness of about 70 or less on the Shore A scale as measured with a durometer.

4. The implantable electrode apparatus according to claim 1 wherein said at least one flexible leg portion includes an aperture on one surface which allows said conductive electrode to contact living tissue.

5. The implantable electrode apparatus according to claim 1 wherein said at least one electrically conductive electrode comprises platinum or a platinum alloy.

6. The implantable electrode apparatus according to claim 1 wherein said at least one electrically conductive electrode comprises iridium or an iridium alloy.

7. The implantable electrode apparatus according to claim 1 wherein said at least one electrically conductive electrode is capable of being operated as an anode, a cathode, or a ground.

8. The implantable electrode apparatus according to claim 1 wherein said at least one lead wire comprises MP35N metal alloy.

9. The implantable electrode apparatus according to claim 1 wherein said at least one lead wire comprises platinum or a platinum metal alloy.

10. The implantable electrode apparatus according to claim 1 wherein said at least one lead wire comprises a stainless steel metal alloy.

11. The implantable electrode apparatus according to claim 1 wherein said body of formed flexible material includes anchor holes.

12. A system for providing blink stimulation of an eyelid, the apparatus comprising:

a body for formed flexible material having at least one flexible leg portion;

at least one electrically conductive electrode that is contained by said at least one flexible leg portion;

at least one lead wire in electrical contact with said at least one electrically conductive electrode;

a pulse generator that is electrically connected to said at least one lead wire; and wherein said pulse generator is mounted on said body.

13. The system of claim 12 wherein said body of formed flexible material comprises silicone having a hardness of about 70 or less on the Shore A scale as measured with a durometer.

14. The system of claim 12 wherein said at least one flexible leg portion comprises silicone having a hardness of about 70 or less on the Shore A scale as measured with a durometer.

15. The system of claim 12 wherein said at least one flexible leg portion comprises an aperture on one surface which allows said conductive electrode to contact living tissue.

16. The system of claim 12 wherein said at least one electrically conductive electrode comprises platinum or a platinum alloy.

17. The system of claim 12 wherein said at least one electrically conductive electrode comprises iridium or an iridium alloy.

18. The system of claim 12 wherein said at least one electrically conductive electrode is capable of being operated as an anode, a cathode, or a ground.

19. The system of claim 12 wherein said at least one lead wire comprises MP35N metal alloy.

20. The system of claim 12 wherein said at least one lead wire comprises platinum or a platinum metal alloy.

21. The system of claim 12 wherein said at least one lead wire comprises a stainless steel metal alloy.

22. The system of claim 12 wherein said body of formed flexible material includes anchor holes.

23. A control system for periodically producing stimulation pulses to an eyelid, said system comprising:

at least one implantable eyelid stimulator having at least one leaflet body and an electode lead body suitable for implantation proximal to an eyelid;

at least one electrode in said at least one leaflet body;

at least one electric pulse generator coupled to said at least one electrode adapted to provide a stimulation pulse; and master control unit means for triggering said at least one electric pulse generator to provide a stimulation pulse to said at least one electrode, wherein said mater control unit means receives signals from a functioning eyelid and transmits signals to trigger said electric pulse generator, aid signal being an RF signal.

24. The control system according to claim 23 wherein said master control unit means for triggering said at least one electric pulse generator is an electric signal generated by a functioning eyelid.

25. The control system according to claim 23 wherein said means master control unit means for triggering to said at least one electric pulse generator is an alternating magnetic field.

26. A control system for periodically roducing stimulation pulses to an eyelid, said system comprising:

at least one implantable eyelid stimulator having at least one leaflet body and an electrode lead body suitable for implantation proximal to an eyelid;

at least one electrode in said at least one leaflet body;

at least one electric pulse generator coupled to said at least one electrode adapted to provide a stimulation pulse; and master control unit means for triggering said at least one electric pulse generator to provide a stimulation pulse to said at least one electrode, wherein said master control unit means receives signals from a functioning eyelid and transmits signals to trigger said electric pulse generator, said signal being a propagated radio signal.

27. The control system according to claim 26 wherein said means for determining when said at least one electric pulse generator will stimulate said at least one electrode is an electric signal generated by a functioning eyelid.

28. The control system according to claim 26 wherein said master control unit means for triggenng to said at least one electric pulse generator is an alternating magnetic field.

29. A method of controlling operation of an implantable electronic device proximal to a nerve in living tissue, said method comprising:

detecting a signal from a functioning eyelid with a first sensing device;

wirelessly transmitting said detected signal to a stimulating device;

generating a stimulating electric signal in said stimulating device in response to said detected signal; and providing said stimulating electric signal to living tissue.

30. The method of claim 29 wherein said transmission to said stimulating device is by RF signal.

31. The method of claim 29 wherein said transmission to said stimulating device is by propagated radio signals.

32. The method of claim 29 wherein said transmission to said stimulating device is by alternating magnetic fields.

33. The method of claim 29 further comprising:

generating a response signal from the stimulated living tissue;

detecting said response signal with a second sensing device;

transmitting said response signal to said stimulating device; and modifying said stimulating electric signal in response thereto.

34. The method of claim 29 wherein said providing said stimulating electric signal comprises responding to a need to cause the eyelid to blink.

35. The method of claim 29 wherein said providing said stimulating electric signal comprises responding to a need to provide a therapeutic electrical stimulation to an eye for beneficial effect on degenerative eye diseases.

* * * * *